(12) United States Patent
Buck

(10) Patent No.: US 9,289,529 B2
(45) Date of Patent: Mar. 22, 2016

(54) ANIMAL SCENT LURE SYSTEMS AND DEVICES

(76) Inventor: John T. Buck, Elmont, NY (US)

(*) Notice: Subject to any disclaimer, the term of this patent is extended or adjusted under 35 U.S.C. 154(b) by 433 days.

(21) Appl. No.: 13/161,784

(22) Filed: Jun. 16, 2011

(65) Prior Publication Data

US 2012/0317863 A1 Dec. 20, 2012

(51) Int. Cl.
| | |
|---|---|
| *A01M 31/00* | (2006.01) |
| *A01M 1/20* | (2006.01) |
| *A01M 31/06* | (2006.01) |
| *A61L 9/12* | (2006.01) |
| *A61L 9/04* | (2006.01) |
| *A24F 25/00* | (2006.01) |
| *A47G 25/00* | (2006.01) |
| *A01M 29/12* | (2011.01) |
| *A47G 25/14* | (2006.01) |
| *A44C 15/00* | (2006.01) |

(52) U.S. Cl.
CPC ............... *A61L 9/12* (2013.01); *A01M 1/2044* (2013.01); *A01M 29/12* (2013.01); *A01M 31/008* (2013.01); *A01M 31/06* (2013.01); *A61L 9/04* (2013.01); *A61L 9/042* (2013.01); *A44C 15/002* (2013.01); *A47G 25/1442* (2013.01)

(58) Field of Classification Search
CPC ... A01M 1/2044; A01M 31/00; A01M 31/06; A01M 31/008; A61L 9/12; A61L 9/125; A61L 9/127; A01K 27/007; Y10T 24/3416; Y10T 24/3449; Y10T 24/3489; Y10T 24/4755; A47G 25/08; A47G 25/14; A47G 25/18; A47G 25/183; A47G 25/28; A47G 25/74; A47G 25/743; A47G 25/746

USPC ........... 239/34, 36, 53, 57, 152, 153; 43/1, 2; 248/74.5, 216.1, 217.3, 205.2, 304, 248/339, 211, 301, 322; 119/653, 654, 758, 119/760, 856; 63/1.15; 24/306, 318, 343, 24/369, 442; 223/85, 86, 88, DIG. 1

See application file for complete search history.

(56) References Cited

U.S. PATENT DOCUMENTS

| | | | | |
|---|---|---|---|---|
| 1,344,318 | A * | 6/1920 | Slye et al. | 239/57 |
| 2,452,424 | A | 10/1948 | Bell | |
| 2,616,759 | A | 11/1952 | Walsh | |
| 2,959,354 | A * | 11/1960 | Beck | 239/36 |
| 3,046,192 | A | 7/1962 | Bilyeu | |
| 4,523,717 | A | 6/1985 | Schwab | |
| 4,682,715 | A * | 7/1987 | Reeves | 222/175 |
| 4,722,477 | A * | 2/1988 | Floyd | 239/36 |
| 4,846,461 | A * | 7/1989 | Robards et al. | 482/72 |
| 4,850,798 | A * | 7/1989 | Bailey | F03D 1/0608 416/11 |
| 5,074,439 | A * | 12/1991 | Wilcox | 222/175 |

(Continued)

*Primary Examiner* — Len Tran
*Assistant Examiner* — Alexander Valvis

(57) ABSTRACT

Animal scent lure systems and devices are provided in which scent element holder devices are employed to removably secure a scent element to an animal decoy, for example, to attract wild animals such as deer. For example, an animal lure device includes a scent element holder device for removably holding an animal scent element. The scent element holder device includes a first connecting element to connect the scent element holder device to a stationary object, a second connecting element for removably securing a scent element to the scent element holder device; and an extension arm element connecting the first and second connecting elements. The extension arm element is adapted to maintain the second connecting element offset from the stationary object (e.g., animal decoy) to which the first connecting element is attached.

9 Claims, 4 Drawing Sheets

(56) References Cited

U.S. PATENT DOCUMENTS

| | | | |
|---|---|---|---|
| 5,148,949 A * | 9/1992 | Luca | 222/175 |
| 5,307,584 A | 5/1994 | Jarvis | |
| 5,622,314 A | 4/1997 | Eason | |
| 5,865,372 A * | 2/1999 | Ceresko | 239/60 |
| 5,899,382 A * | 5/1999 | Hayes et al. | 239/56 |
| 5,987,800 A * | 11/1999 | Regan | 43/1 |
| 6,038,804 A * | 3/2000 | Cuerrier | 43/1 |
| 6,126,085 A * | 10/2000 | Wanzenbock | 239/36 |
| 6,158,668 A | 12/2000 | Burgeson | |
| 6,340,120 B1 | 1/2002 | Seymour | |
| 6,398,126 B1 * | 6/2002 | Pitchford | 239/36 |
| 6,588,440 B2 * | 7/2003 | Varnado | 135/90 |
| 6,676,033 B1 * | 1/2004 | Campesi, Sr. | 239/44 |
| 6,764,656 B1 * | 7/2004 | Matulevich | 422/124 |
| 6,786,424 B1 * | 9/2004 | Ward | 239/36 |
| 6,857,579 B2 | 2/2005 | Harris | |
| 7,086,635 B1 * | 8/2006 | Drapeau | 248/339 |
| 7,093,770 B1 * | 8/2006 | Moran | 239/36 |
| 7,121,475 B2 * | 10/2006 | Thomas | 239/53 |
| 7,222,762 B2 * | 5/2007 | Rees et al. | 224/148.4 |
| 7,611,034 B1 * | 11/2009 | Peterson | A47G 25/743 |
| | | | 211/115 |
| 7,874,093 B2 * | 1/2011 | Rohrke | 43/2 |
| 7,988,984 B2 * | 8/2011 | Hockaday | 424/403 |
| 8,146,836 B2 * | 4/2012 | Hogan | 239/36 |
| 2002/0108976 A1 * | 8/2002 | Carmichael | A47G 25/16 |
| | | | 223/85 |
| 2003/0145506 A1 | 8/2003 | Lorenz | |
| 2006/0169793 A1 * | 8/2006 | Price et al. | 239/34 |
| 2006/0249549 A1 * | 11/2006 | Giampavolo | A47G 25/1442 |
| | | | 223/85 |
| 2006/0289668 A1 * | 12/2006 | Szymczak et al. | 239/36 |
| 2007/0080181 A1 * | 4/2007 | Lynch | A47G 25/005 |
| | | | 223/85 |
| 2009/0050711 A1 * | 2/2009 | Castner | 239/152 |
| 2009/0145938 A1 * | 6/2009 | Kahn | 224/183 |
| 2009/0179082 A1 * | 7/2009 | Price et al. | 239/36 |

* cited by examiner

ANIMAL SCENT LURE SYSTEMS AND DEVICES

TECHNICAL FIELD

This invention relates generally to animal scent lure systems and devices and, more specifically, to a scent element holder device that is used by hunters to removably secure a scent element to an animal decoy, for example, to attract wild animals such as deer.

BACKGROUND

In general, hunters of deer and other wild game animals will typically utilize some type of animal lure device to lure game animals, such as deer, to a hunting area. One type of lure commonly employed by hunters includes a scented substance having an odor that serves as an animal attractant. These scents typically include urine from the hunted animal, or estrus scent, and such scented lures are typically available in liquid concentrated form. These lure scents may be dispensed in the hunting area in various manners.

For example, the scent may be stored in a sealed container and dispensed from the container at the hunt site, wherein the scent is applied directly to the boots of the hunter, or sprayed or otherwise applied onto some local object such as the ground, or a decoy, or some scent pad that is attached to a tree or branch, etc., in the hunting area. Alternatively, a scent container may contain a wick that is stored in the container and soaked in the scent, whereby the wick is deployed from the container and suspended from a tree or bush at the hunt site.

Other animal lure devices commonly used by hunters include decoy devices. For instance, deer hunters typically use a variety of three-dimensional deer decoys to attract the attention of live Whitetail deer, and lure the deer in close proximity for an ideal, ethical shot, by using sight. When a whitetail deer sees a deer decoy, it believes the decoy is another whitetail deer and to confirm the sighting, the deer will start approaching the decoy to scent check the decoy for verification. A whitetail deer will scent check by putting its nose close to what is known as a "tarsal" gland. All deer have two tarsal glands, each of which being located on the inside rear legs of the deer at the knuckle/joint. The tarsal glands are typically 2-3 inches by 2-3 inches in area (i.e., in the range of about 4 to 9 square inches in area) depending on the size and age of the deer.

The tarsal gland is the most important gland to whitetailed deer. The tarsal gland is used by a deer to recognize another deer and deer often sniff each other's tarsal glands. By doing so, a deer can determine the sex, dominant and social status, and reproductive condition of another deer in the herd. In particular, bucks rely on their nose to identify possible threats, such as a hunter or a predator, or to hunt for a receptive doe during the rut, and to identify one particular deer from another. All deer, bucks and does, adults and fawns, urinate onto the tarsal gland in a behavior called "rub urination." The urine that remains on the gland undergoes some reactions with the air and with bacteria to produce the gland's characteristic smell. Deer urinate on these glands at all times of the year. Typically, the urine is licked off the gland.

However, during the breeding season, the males and primarily dominant or mature males, urinate onto the tarsal gland more frequently, and do not lick the excess urine off the gland, which stains the gland dark and gives the buck a rutting odor.

All deer including bucks and does use the same behavior and gland for identification purposes. However, during the rut, the activity surrounding the identifying gland is greatly increased. Does will have their glands give off the estrous odor to signify to a buck at what stage they are ready for breeding. Does will identify their fawns through the smell of their tarsal gland. Bucks use the gland to advertise their dominant status and breeding condition, both to other bucks and does.

SUMMARY OF THE INVENTION

Exemplary embodiments of the invention generally include animal scent lure systems and devices and, more specifically, scent element holder devices that are used by hunters to removably secure a scent element to an animal decoy, for example, to attract wild animals such as deer.

In one exemplary embodiment of the invention, an animal lure device includes a scent element holder device for removably holding an animal scent element. The scent element holder device includes a first connecting element to connect the scent element holder device to a stationary object, a second connecting element to removably secure a scent element to the scent element holder device, and an extension arm element connecting the first and second connecting elements. The extension arm element is adapted to maintain the second connecting element offset from a stationary object to which the first connecting element is attached.

The first connecting element may be formed of a closed loop element, which insertably receives a strap element that is passed through the closed loop element to secure the scent element holder device to the stationary object. The strap element may be a Velcro strap. The first connecting element may include friction elements formed on a surface thereof to frictionally engage the stationary object. The friction elements may be raised ridges that are formed on a planar surface of the first connecting element.

The second connecting element may be a hook-shaped element forming an open loop structure to securely hold a scent element. The second connecting element may be formed of a clamp element to securely hold a scent element A scent element that is removably connectable to the second connecting element may be a scent wick, a scent canister, or a scent wafer.

In another exemplary embodiment of the invention, an animal lure system includes an animal decoy, and an animal lure device disposed on the animal decoy at an anatomically correct position of a scent gland located on an animal simulated by the animal decoy. The animal lure device is adapted to emit a scent that simulates a scent emitted by the scent gland of the animal. For example, the animal decoy may be a deer decoy, wherein the animal lure device is disposed on a rear leg of the animal decoy in an anatomically correct position of tarsal gland of a deer. The animal lure device may include a removable scent element holder device that holds a removable animal scent element.

These and other aspects, features and advantages of the present invention will become apparent from the following detailed description of preferred embodiments, which is to be read in conjunction with the accompanying figures.

DETAILED DESCRIPTION OF EXEMPLARY EMBODIMENTS

Exemplary embodiments of the invention will now be described in further detail with reference to animal scent lure systems and devices and, more specifically, to scent element holder devices that are used by hunters to removably secure a scent element to an animal decoy, for example, to attract wild animals such as deer. It is to be understood, however, that the techniques of the present invention are not limited to the devices and methods shown and described herein. Modifications to the illustrative embodiments will become apparent to those of ordinary skill in the art.

Figure 1:
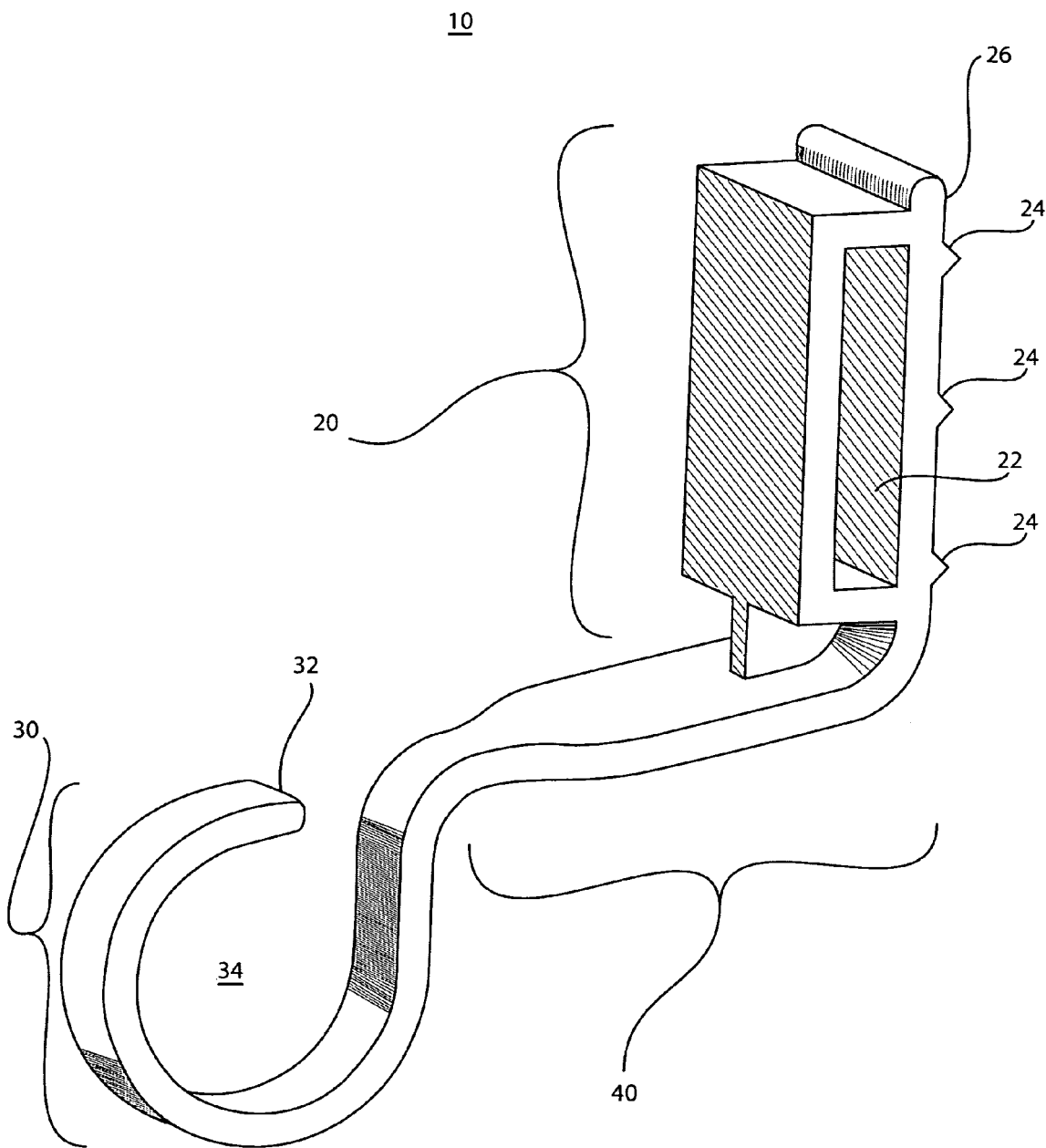
FIG. 1 is a perspective view of a scent element holder device according to an exemplary embodiment of the invention.
Figure 2:
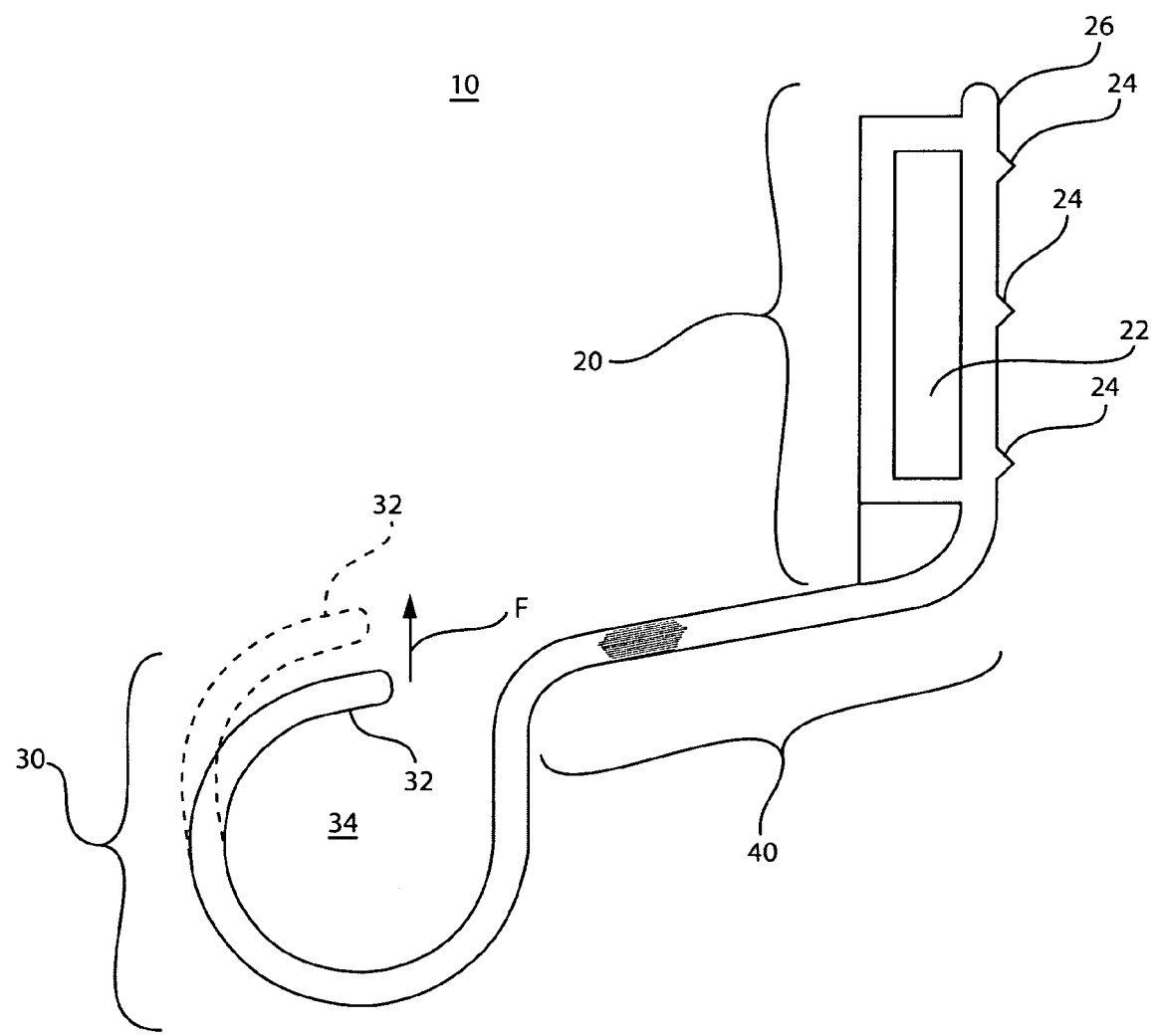
FIG. 2 is a side view of the scent element holder device of FIG. 1 according to an exemplary embodiment of the invention.

FIGS. 1 and 2 illustrate a scent element holder device (10) for removably holding an animal scent element according to an exemplary embodiment of the invention. In particular, FIG. 1 is a perspective view of the scent element holder device (10) and FIG. 2 is a side view of the scent element holder device (10) of FIG. 1, according to an exemplary embodiment of the invention. Referring collectively to FIGS. 1 and 2, the scent element holder device (10) comprises a first connecting element (20) to connect the scent element holder device (10) to a stationary object (e.g., animal decoy, tree, bush, branch, etc.), a second connecting element (30) to removably secure a scent element to the scent element holder device (10), and an extension arm element (40) connecting the first (20) and second (30) connecting elements. The extension arm element (40) is adapted (via shape, size and position) to maintain the second connecting element (30) at some point offset from the stationary object to which the first connecting element (20) is attached. As shown in FIGS. 1 and 2, in one exemplary embodiment of the invention, a longitudinal axis of the extension arm element (40) extends substantially orthogonal to a plane or longitudinal axis of the first connecting element (20) to maintain the second connecting element (30) offset from the first connecting element (20).

In one exemplary embodiment as shown in FIGS. 1 and 2, the first connecting element (20) comprises a closed loop element forming a closed aperture (22) to insertably receive a strap element that is passed through the closed aperture (22) to secure the scent element holder device (10) to a stationary object such as a tree branch, or bush or animal decoy, for example. The strap element may be a strap with a hook and pile connector (e.g., VELCRO) strap, or some other mechanism such as a string or strapping material that can be inserted through the aperture (22) and wrapped around some stationary object to secure the device (10) to the stationary object.

As further depicted in FIGS. 1 and 2, the first connecting element (20) comprises friction elements (24) formed on a back surface (26) thereof to frictionally engage the stationary object. In one exemplary embodiment, the friction elements (24) include raised ridge elements that are formed on a planar back surface (26) of the first connecting element (20). The friction elements (24) are adapted to dig into a surface of the stationary object due to force exerted when the first connecting element (20) is tied or strapped or otherwise secured to the stationary object.

As further depicted in FIGS. 1 and 2, the second connecting element (30) is hook-shaped (or loop-shaped) having open tip end (32) to receive a scent element that may be removably connected to the second connecting element (30). Various types of scent elements may be employed with the scent element holder device (10) according to exemplary embodiments of the invention. For instance, scent elements for use with the scent element holder device (10) include, but are not limited to, conventional and proprietary scent wicks, scent canisters, and scent wafers.

The scent element holder device (10) can be made of any suitable material such as plastic, plastic composite materials, or metallic materials, to provide a rigid or semi rigid structure. For example, in one exemplary embodiment, the device (10) is made of flexible plastic which allows the second connecting element (30) to be flexible and hold other non-conventional scent elements by a clamping force. For instance, as shown in FIG. 2, a force (indicated by arrow F) can be applied (via a person's fingers) to the tip end (32) of the second connecting element (30) to enlarge an inner loop region (34) and allow an actual scent gland, e.g., tarsal gland of a deer, to be inserted within the enlarged inner loop region (34). When the force is ended, the tip end (32) will spring back into place, thereby exerting a clamping force on the actual scent gland, and thus securely holding the scent gland in place within the inner loop region (34) of the second connecting end (30).

It is to be understood that various other structures may be used to implement the first and second connecting elements (20) and (30) shown in FIGS. 1 and 2. For instance, the second connecting element (30) may be implemented using a clamp connector structure (similar to a clothespin for example) having a pair a clamping edges with a clamping force exerted by use of a spring element. The clamping element can be used to clamp connecting ends of scent elements (e.g., looped ends) or clamp down on actual scent glands of the target animal.

Figure 3:
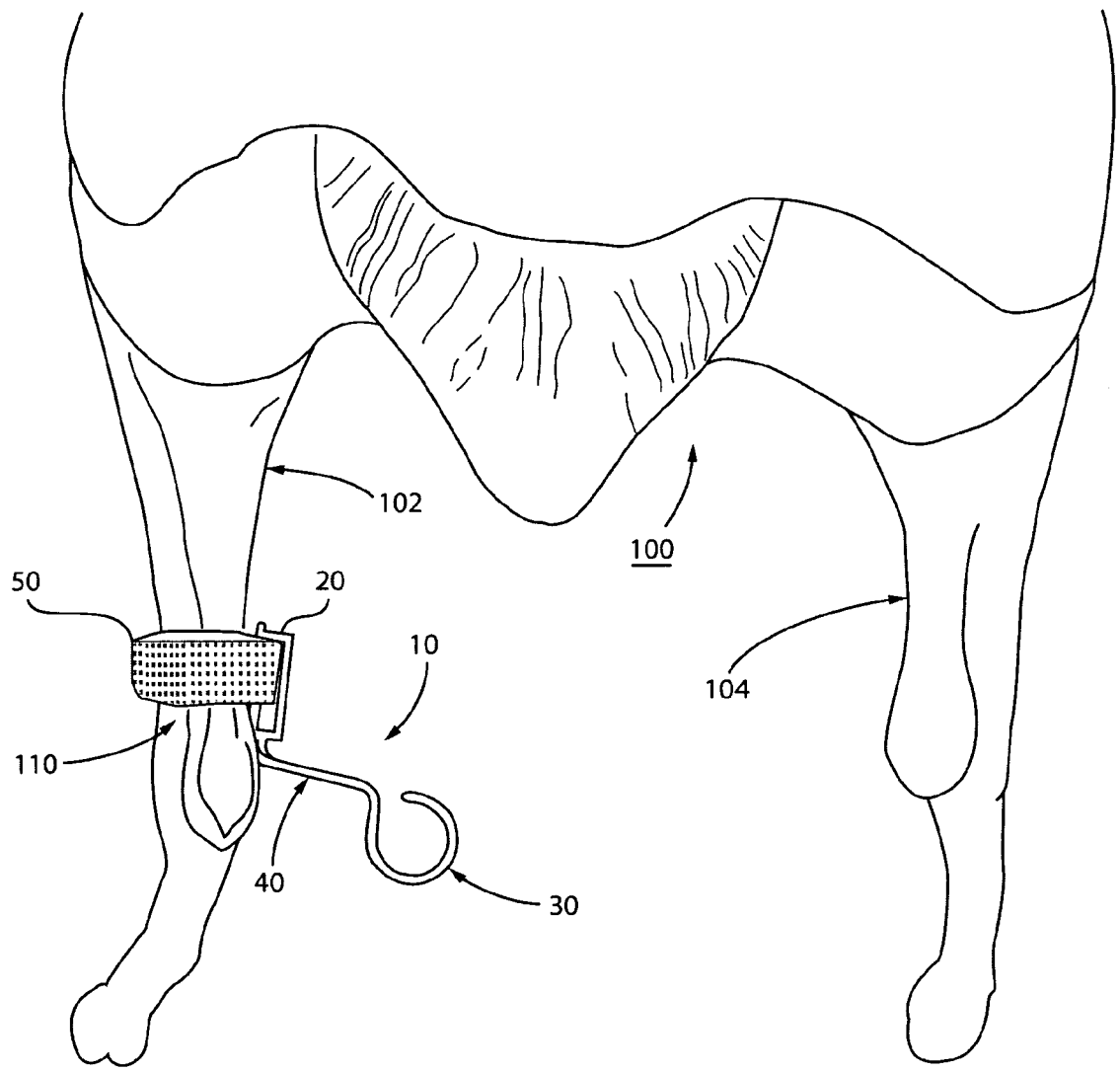
FIG. 3 is an animal lure system that includes an animal decoy and a scent element holder device according to an exemplary embodiment of the invention.
Figure 4:
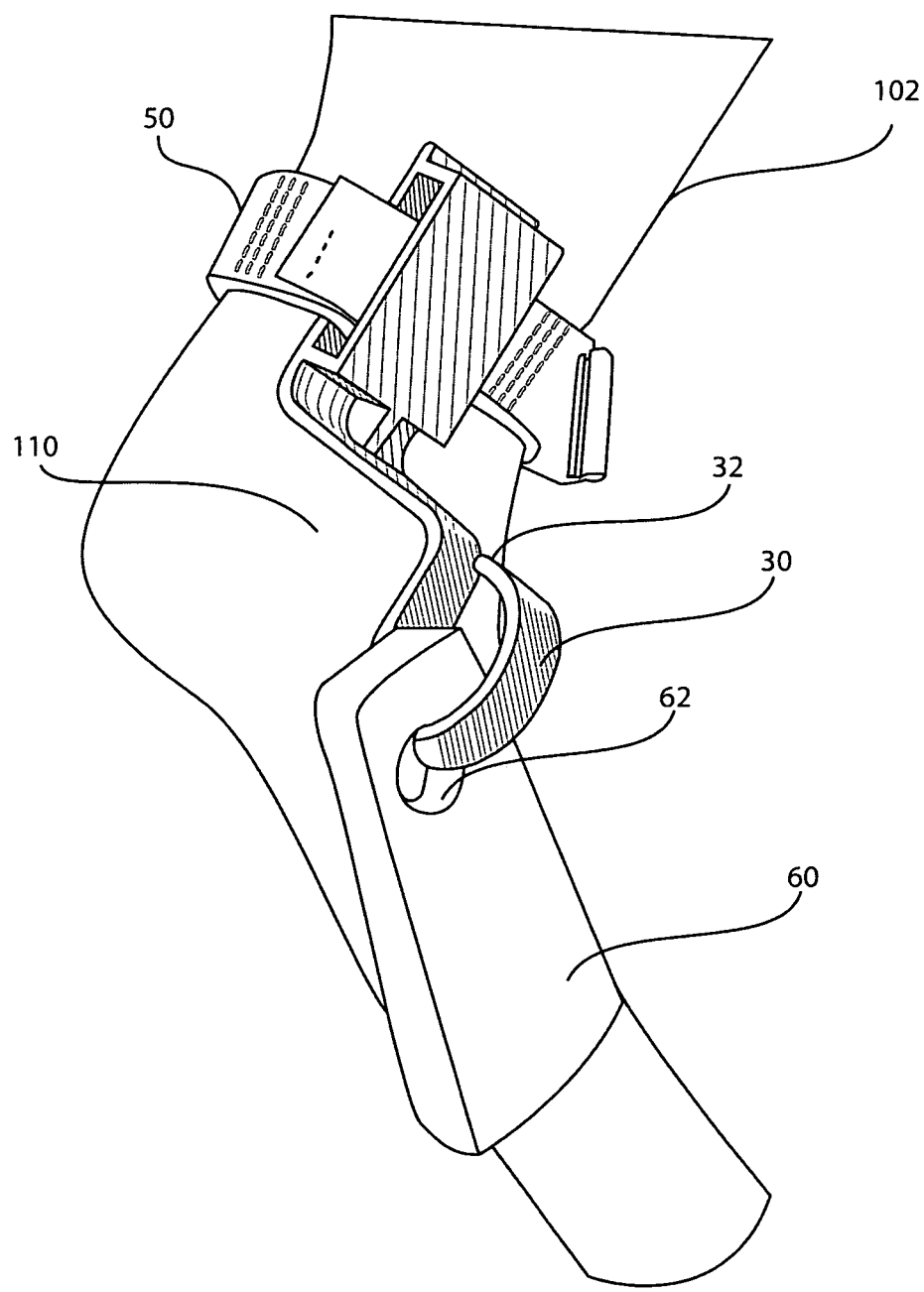
FIG. 4 is an enlarged view of the scent holder device shown in FIG. 3 being disposed in an anatomically correct position of a scent gland on a leg of the animal decoy device, according to an exemplary embodiment of the invention.

It is to be appreciated that the exemplary scent element holder device (10) shown in FIGS. 1 and 2 may be used in conjunction with an animal decoy to provide an animal lure system that is useable by hunters for luring wild animals. For example, FIGS. 3 and 4 illustrate an exemplary animal lure system that includes an animal decoy (100) and a scent holder device (10) according to an exemplary embodiment of the invention. In the exemplary embodiment of FIGS. 3 and 4, the animal decoy (100) is a three-dimensional deer decoy, wherein FIG. 3 illustrates a rear end of the deer decoy (100) showing the rear left (102) and right (104) hind legs. FIG. 3 further illustrates the scent holder device (10) being securely disposed on the left hind leg (102) of the decoy (100) using a Velcro strap (50) that encompasses the leg (102), as the Velcro is folded back on itself with a tip of the strap (50) inserted through the aperture (22) of the first connecting element (20).

FIG. 4 is an enlarged view of the scent holder device (10) shown in FIG. 3 having a scent wick (60) connected to the second connecting element (30) of the scent holder device (10). As shown in FIG. 4, the scent wick (60) includes an aperture (62) through which the open end (32) of the second connecting element (30) is inserted to hang the scent wick (60) on the hook-shaped connecting element (30).

It is to be appreciated that the animal lure system of FIGS. 3 and 4 allows the scent element holder device (10) and scent element (60) to be disposed at an anatomically correct position of a scent gland on a leg of the animal decoy device, according to an exemplary embodiment of the invention. In particular, in the exemplary embodiment of FIGS. 3 and 4, the scent holder device (10) and scent element (60) are disposed in an anatomically correct position on the rear leg (102) of the deer decoy (100) near a tarsal gland (110) of a deer. With an exemplary lure system of FIGS. 3 and 4 where the animal lure device (e.g., combination holder device (10) and scent element (60)) is disposed on the animal decoy (100) at an anatomically correct position of a tarsal gland (110), the animal lure device is advantageously adapted to emit a scent that simulates a scent emitted by the scent gland (e.g., tarsal gland) of the particular animal (e.g., deer) simulated by the decoy (100).

During a hunting trip, a hunter can attach the scent holder device (10) to an anatomically correct position (tarsal gland position) on the rear leg of the deer decoy (fastened by, e.g., a Velcro polypropylene strap) and connect a scent element on the hook-shaped arm which simulates the scent emitted by a tarsal gland. The hook-shaped connecting element (30) of the device (10) will allow all felt scent wicks, plastic wick devices that hold felt and hard ring type scent devices to be held in place, preventing the wind from blowing the scent device away, while allowing the wind to blow scent that is emitted from the scent element (60) toward the deer more effectively. Indeed, because the scent element freely hangs on the hook-shaped connecting element (30) at a position offset and away from the stationary object (e.g., leg of deer decoy), the scent holder device (10) will allow any scent element to practically hang in mid-air, taking advantage of the wind currents. Because deer use the tarsal gland for identification purposes, they know that by the smell of the scent being used to attract the deer and where it is properly located, they are less likely to be spooked from the location and to have their attention divided.

A scent holder device and animal lure system implementing a scent holder device according to principles of the invention as discussed above provide many advantages over conventional animal lure systems, devices and methods. For instance, the use of a scent holder device and scent element according to principles of the invention will obviate the need for hunters to spray animal lure scent directly on an animal decoy, causing that particular odor to foul and contaminate the decoy when not washed off properly after the hunt is complete. Indeed, it is considered poor practice to apply, e.g., deer sex attractant scent directly onto a deer decoy as this will contaminate the decoy, as the scent will become foul and alarm deer during subsequent use of the decoy.

An exemplary scent holder device as described herein can be used with any type of scent element including, but not limited to, scent wicks, scent canisters, and scent wafers, and allow such scent elements to be held securely in an anatomically correct location on an animal decoy near a scent gland which the target game animal is familiar with (e.g., tarsal glands on rear hind legs of deer). The scent elements can be used in conjunction with various types of scents that are suitable for the given animal being hunted. For instance, a scent wick made of felt can be whetted with deer urine to implement attractive scent.

Moreover, principles of the invention improve scent dispersion in the area where deer are located, so they can smell any scent emitted by a scent element used with the scent holder device. Indeed, principles of the invention obviate the need for hunters to place scent canisters on the ground, in close vicinity of the decoy, wherein the scent can be prevented from being readily blown and airborne through the lack of air currents or blocked by any vegetation on the ground. Instead, by using a scent element in conjunction with a scent element holder device as described herein, wind currents will wafer the scent more efficiently because the scent element is held in midair, whereby wind may readily blow the handing scent element on both sides thereof, or through any wafer to dispense the luring scent at greater distances, helping to attract deer more successfully.

Although exemplary embodiments of the present invention have been described herein with reference to the accompanying figures, it is to be understood that the invention is not limited to those precise embodiments, and that various other changes and modifications may be made therein by one skilled in the art without departing from the scope of the appended claims.

What is claimed is:

1. An animal lure device, comprising:
   a scent element holder device comprising:
      a first connecting element to connect the scent element holder device town object, wherein the first connecting element comprises a rectangular-shaped closed loop element to insertably receive a strap element that is passed through said rectangular-shaped closed loop element to secure the scent element holder device to the object;
      a second connecting element configured to removably hold different types of animal scent elements, wherein the different types of animal scent elements comprise a scent wick and an animal scent gland; and
      an extension arm element connecting the first and second connecting elements, wherein the extension arm element is adapted to maintain the second connecting element offset from the object to which the first connecting element is attached,
      wherein the first connecting element, the second connecting element and the extension arm element are integrally formed as one piece of molded plastic material;
      wherein the first connecting element and the extension arm element are elongated elements that extend at an angle in relation to each other, wherein the angle is a non-straight angle; and
      wherein the second connecting element comprises a flexible hook-shaped member having a tip end, wherein the tip end is configured for insertion through an aperture of the scent wick type of animal scent element, and wherein the flexible hook-shaped member is flexibly configured to allow the tip end to be resiliently pulled from a first position to a second position to increase a size of an inner region of the flexible hook-shaped member and then released so that the tip end springs back to the first position to securely hold the animal scent gland type of animal scent element within the inner region of the flexible hook-shaped member.

2. The device of claim 1, wherein the strap element comprises a hook-and-loop fastener.

3. The device of claim 1, wherein the first connecting element comprises friction elements formed on a surface thereof to frictionally engage the object.

4. The device of claim 3, wherein the friction elements comprise raised ridges that are formed on a planar surface of the first connecting element.

5. The device of claim 1, further comprising an animal scent element that is removably connectable to the second connecting element.

6. The device of claim 5, wherein the animal scent element is a scent wick.

7. The device of claim 5, wherein the animal scent element is a scent canister.

8. The device of claim 5, wherein the animal scent element is a scent wafer.

9. The device of claim 1, wherein the first connecting element and the extension arm element are substantially orthogonal to each other.

* * * * *